US010420905B2

(12) United States Patent
Jackson

(10) Patent No.: US 10,420,905 B2
(45) Date of Patent: Sep. 24, 2019

(54) CPR TEMPLATE

(71) Applicant: The CPR Lifewrap LLC, Chattanooga, TN (US)

(72) Inventor: Felicia Jackson, Hixon, TN (US)

(73) Assignee: THE CPR LIFEWRAP LLC, Chattanooga, TN (US)

( * ) Notice: Subject to any disclaimer, the term of this patent is extended or adjusted under 35 U.S.C. 154(b) by 775 days.

(21) Appl. No.: 15/091,361

(22) Filed: Apr. 5, 2016

(65) Prior Publication Data

US 2016/0300507 A1    Oct. 13, 2016

Related U.S. Application Data

(60) Provisional application No. 62/144,874, filed on Apr. 8, 2015.

(51) Int. Cl.
*G09B 23/28*     (2006.01)
*A61M 16/00*     (2006.01)
*A61H 31/00*     (2006.01)
*A61H 99/00*     (2006.01)

(52) U.S. Cl.
CPC ....... *A61M 16/0048* (2013.01); *G09B 23/288* (2013.01); *A61H 31/005* (2013.01); *A61H 31/007* (2013.01); *A61H 99/00* (2013.01); *A61H 2201/165* (2013.01); *A61H 2201/1619* (2013.01); *A61H 2201/5043* (2013.01)

(58) Field of Classification Search
USPC ................ 434/262, 265, 267, 269, 272, 275
See application file for complete search history.

(56) References Cited

U.S. PATENT DOCUMENTS

| | | | | |
|---|---|---|---|---|
| 4,050,457 A | * | 9/1977 | Davidson | A61M 16/0048 128/202.28 |
| 4,802,857 A | * | 2/1989 | Laughlin | G09B 23/288 434/265 |
| 5,088,485 A | * | 2/1992 | Schock | A61M 16/0048 128/202.28 |
| 6,427,685 B1 | * | 8/2002 | Ray, II | G09B 23/288 128/200.24 |
| 7,223,103 B2 | * | 5/2007 | Cantrell | G09B 23/288 434/262 |
| 2011/0247963 A1 | * | 10/2011 | Stockett | G09B 23/288 206/572 |
| 2012/0100516 A1 | * | 4/2012 | Iwami | G09B 23/288 434/265 |
| 2015/0187230 A1 | * | 7/2015 | Doad | G09B 23/288 434/265 |
| 2015/0228205 A1 | * | 8/2015 | Koskimaki | G09B 23/288 600/301 |
| 2015/0279237 A1 | * | 10/2015 | Sugiyama | G09B 23/288 434/265 |

* cited by examiner

*Primary Examiner* — Kurt Fernstrom
(74) *Attorney, Agent, or Firm* — Luedeka Neely Group, PC

(57) ABSTRACT

A CPR template for use by a rescuer in performing CPR includes a pliable mask portion, a pliable body portion and a connecting link that joins the mask portion to the body portion. The mask portion is adapted to be placed over the face of a person, and includes a mouthpiece extending therethrough for use in administering rescue breaths. The body portion has a sternal diagram displayed thereon, and an instructional area in which CPR instructions are displayed.

14 Claims, 3 Drawing Sheets

CPR TEMPLATE

CROSS-REFERENCE TO RELATED APPLICATION

This application claims the benefit of U.S. Provisional Patent Application No. 62/144,874, which was filed on Apr. 8, 2015.

FIELD OF THE INVENTION

This invention relates to an aid to facilitate the correct application of cardiopulmonary resuscitation ("CPR") to a human patient.

BACKGROUND OF THE INVENTION

CPR is a lifesaving technique that is useful in many emergencies in which a human patient's breathing and/or heartbeat has stopped, including heart attack or near drowning. When the heart stops, the lack of oxygenated blood can cause brain damage in only a few minutes. A person may die within eight to ten minutes. CPR can keep oxygenated blood flowing to the patient's brain and other vital organs until more definitive medical treatment can restore a normal heart rhythm.

If a patient is encountered whose breathing and/or heartbeat has stopped, the American Heart Association recommends that CPR be begun with 30 chest compressions. Then, it is recommended that the patient's airway be checked, and the rescuer begin to give rescue breaths. This recommendation applies to adults, children and infants needing CPR, but not newborns.

Before starting CPR, a rescuer should check to determine if the patient is conscious or unconscious. If the patient appears to be unconscious, the rescuer should tap or shake his or her shoulder and ask loudly, "Are you OK?" If the patient doesn't respond and two people are available, one should call 911 or the local emergency number and one should begin CPR. If a rescuer is alone and has immediate access to a telephone, he or she should call 911 before beginning CPR, unless it is believed that the patient has become unresponsive because of suffocation (such as from drowning). If this is the case, CPR should be begun for one minute before the 911 (or local emergency) call is placed. If an automated external defibrillator ("AED") is available, the American Heart Association recommends that one shock be delivered per the instructions on the device before CPR is begun.

The American Heart Association uses the acronym CAB, for "compressions, airway, breathing" to help people remember the order to perform the steps of CPR. The purpose of "compressions" is to restore blood circulation. The first step is to place the patient on his or her back on a firm surface. Then for an adult patient, the rescuer should kneel next to the patient's neck and shoulders, and place the heel of one hand over the center of the patient's chest, between the nipples. The rescuer should then place his or her other hand on top of the first hand, keeping his/her elbows straight and positioning his/her shoulders directly above the hands on the patient's chest. The rescuer should then use his/her upper body weight to push straight down on (compress) the chest by at least 2 inches (approximately 5 centimeters). Compression should be carried out at a rate of about 100 compressions per minute. If the rescuer hasn't been trained in CPR, the American Heart Association recommends that he/she continue chest compressions without initiating rescue breathing until there are signs of movement or until emergency medical personnel take over. If the rescuer has been trained in CPR, he/she should proceed to checking the airway and initiating rescue breathing.

After a rescuer who has been trained in CPR has performed 30 chest compressions, he/she should open the patient's airway using a head-tilt, chin-lift maneuver. This requires the rescuer to put his/her palm on the patient's forehead and gently tilt the patient's head back. Then with the other hand, the rescuer should gently lift the patient's chin forward to open the airway. The rescuer should then check for normal breathing, taking no more than 5-10 seconds to do so. The rescuer should look for chest motion, listen for normal breath sounds, and feel for the patient's breath on the rescuer's cheek or ear. Gasping by the patient is not considered to be normal breathing. If the patient isn't breathing normally, mouth-to-mouth breathing for the patient should be begun.

Rescue breathing can be mouth-to-mouth breathing or mouth-to-nose breathing if the mouth is seriously injured or can't be opened. With the airway open (using the head-tilt, chin-lift maneuver), the rescuer should pinch the nostrils of the patient shut for mouth-to-mouth breathing and cover the patient's mouth with his/her own making a seal. The rescuer should give a first rescue breath, lasting about one second, and then watch to see if the patient's chest rises. If it does rise, the rescuer can proceed with a second breath. If the patient's chest doesn't rise, the rescuer should repeat the head-tilt, chin-lift maneuver before giving the second breath. Thirty chest compressions followed by two rescue breaths is considered one CPR cycle. If the patient has not responded after five cycles (about two minutes) and an AED is available, it should be applied pursuant to the directions and prompts provided by the device. The rescuer should administer one shock, then resume CPR, starting with chest compressions, for two more minutes before administering a second shock. The rescuer should continue CPR until there are signs of movement or until emergency medical personnel arrive.

The procedure for giving CPR to a child between the ages of one and eight is essentially the same as that for an adult. However, if the rescuer is alone, he/she should perform five cycles of compressions and breaths on the child, taking about two minutes, before calling 911 or using an AED. The rescuer should only use one hand to perform chest compressions, and he/she should breathe more gently. The same compression-breath rate should be used as is used for adults, 30 compressions followed by two breaths comprising one cycle. Following the two breaths, the rescuer should immediately begin the next cycle of compressions and breaths. After five cycles (about two minutes) of CPR, if there is no response and an AED is available, it should be applied pursuant to the directions and prompts provided by the device. The rescuer should use pediatric defibrillator pads, if available, for children ages one through eight. If pediatric pads aren't available, adult pads may be used. After one shock has been administered, CPR should be resumed, starting with chest compressions, for two more minutes before administering a second shock. CPR should be continued until the child moves or help arrives.

For infants (i.e., children less than one year old), the rescuer should first stroke the baby and watch for a response, such as movement. The baby should not be shaken. Since most cardiac arrests in babies occur from lack of oxygen such as from drowning or choking, the rescuer should look for an airway obstruction, or perform first aid for choking. If no obstruction is found, CPR should be begun. If the rescuer is alone, CPR should be conducted for five cycles, about two minutes, before calling 911 or a local emergency number. The baby should be placed on his or her back on a firm, flat surface, such as a table or floor. Imagining a transverse line drawn between the baby's nipples, the rescuer should place two fingers of one hand just below this imaginary line, in the center of the chest, and gently compress the chest about 1.5 inches (about 4 centimeters). The rescuer should continue chest compressions at a rate of 100 compressions per minute. After 30 compressions, the rescuer should gently tip the baby's head back by lifting the chin with one hand and pushing down on the forehead with the other hand. Within no more than about 10 seconds, the rescuer should put his/her ear near the baby's mouth and check for breathing. The rescuer should look for chest motion, listen for breath sounds, and feel for breath on his/her cheek and/or ear. If breathing is not detected, the rescuer should cover the baby's mouth and nose with his/her mouth and using the strength of his/her cheeks, deliver a gentle puff of air (instead of a deep breath from his/her lungs) to slowly breathe into the baby's mouth one time, taking one second for the breath. If the baby's chest rises, a second rescue breath may be given. If the baby's chest does not rise, the head-tilt, chin-lift maneuver should be repeated before the second breath is given. If the baby's chest still doesn't rise, the rescuer should examine the baby's mouth to make sure that no foreign material is inside. If an object is seen, the mouth should be swept by the rescuer with his/her finger. If the airway seems blocked, first aid for a choking baby should be performed. Two breaths should be given after every 30 chest compressions, and CPR should be continued until the baby responds or until medical personnel arrive.

As can be appreciated, the instructions for CPR are somewhat complicated, and they may be hard for a rescuer to remember in an emergency situation. In addition, some potential rescuers are reluctant to make direct mouth-to-mouth contact with a stranger. It would be desirable if an inexpensive device could be provided that would make it easy for a rescuer to perform CPR.

ADVANTAGES OF THE INVENTION

The invention provides a template that makes it easy for a rescuer to begin and carry out CPR in a safe manner. Other advantages and features of this invention will become apparent from an examination of the drawings and the ensuing description.

NOTES ON CONSTRUCTION

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

SUMMARY OF THE INVENTION

The invention comprises a CPR template for use by a rescuer in performing CPR. This template includes a pliable mask portion, a pliable body portion and a connecting link that joins the mask portion to the body portion. The mask portion is adapted to be placed over the face of a person, and includes a mouthpiece extending therethrough for use in administering rescue breaths. The body portion has a sternal diagram displayed thereon, and an instructional area in which CPR instructions are displayed.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DETAILED DESCRIPTION OF THE PREFERRED EMBODIMENTS

Figure 1:
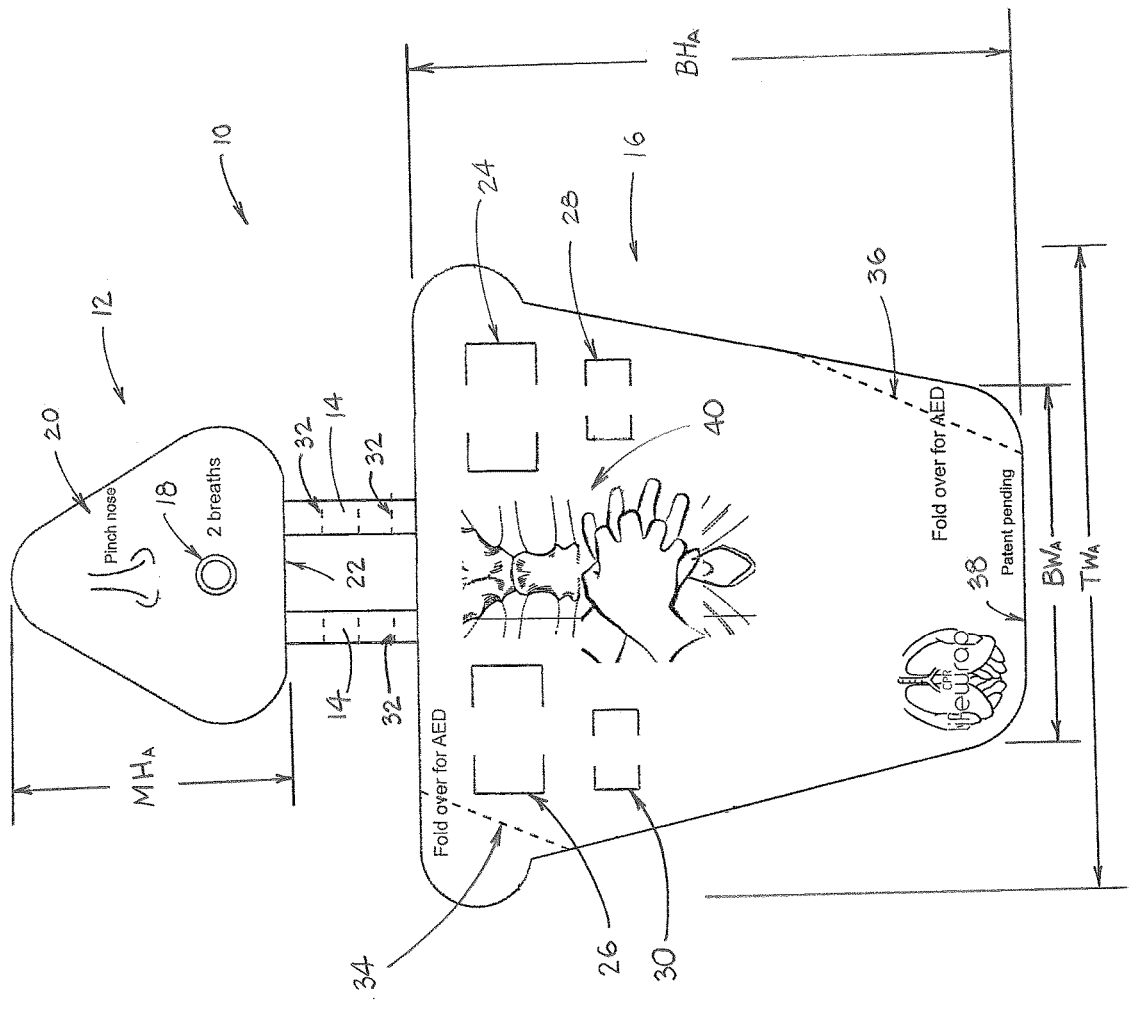
FIG. 1 is a top view of a CPR template for an adult.
Figure 2:
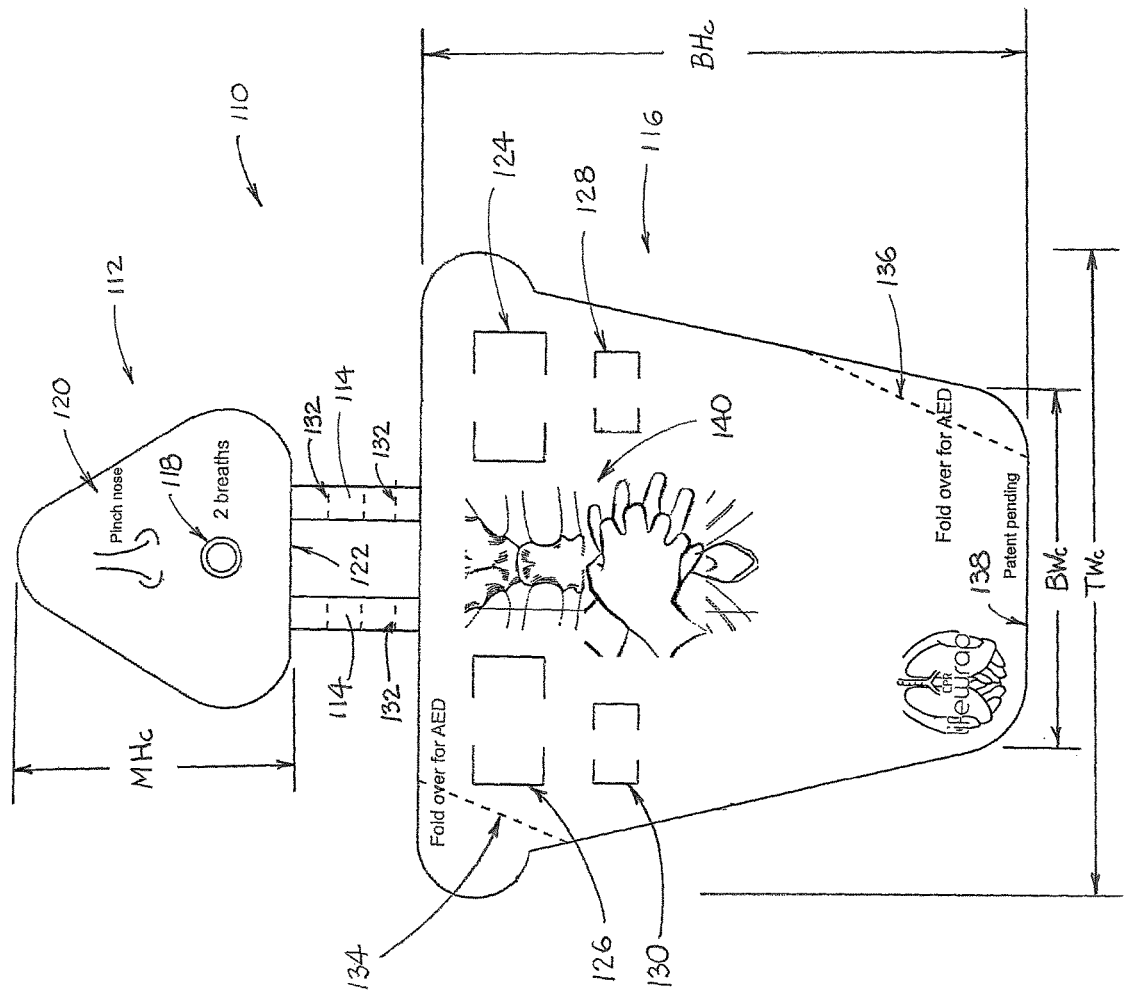
FIG. 2 is a top view of a CPR template for a child.
Figure 3:
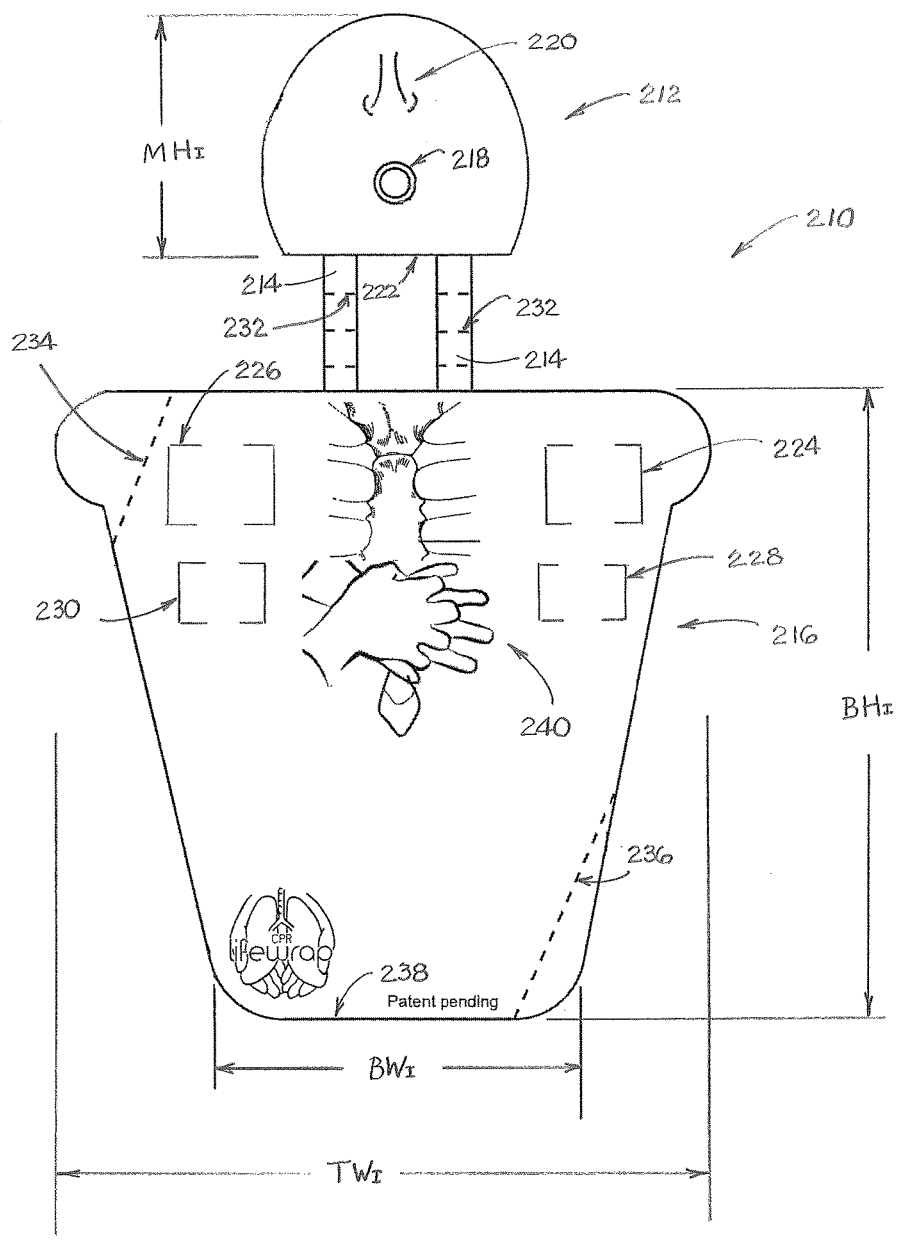
FIG. 3 is a top view of a CPR template for an infant.

As shown in the drawings the invention comprises a CPR template such as template 10 for adults, template 110 for children and template 210 for infants. Referring now to FIG. 1, preferred adult template 10 comprises generally triangular mask portion 12, one or more connecting links 14 (two are preferred) and a generally trapezoidal body portion 16. A conventional mask mouthpiece 18 is mounted in mask portion 12, and above that is located a "nose pinch" instruction/reminder 20. Preferably, mouthpiece 18 is located about 2 inches from baseline 22 of mask portion 12. It is also preferred that "nose pinch" instruction/reminder 20 is located so as to align with the nose of a typical adult when the valve is aligned with the patient's mouth, or at about 3 inches above mouthpiece 18. It is also preferred that CPR instructions such as the following are printed or displayed in instruction areas 24 and 26 on body portion 16:

CPR Instructions
1. Call 911/Get Help.
2. Check for pulse/breathing.
3. No breathing/pulse—Start CPR.
Lay patient down on flat, hard surface
30 compressions 2.0 inches deep, fast and hard
Tilt head, lift chin, pinch nose
Slowly blow into mouth twice until chest rises
Repeat 30 compressions to 2 breaths
Continue until help arrives It is also preferred that template placement instructions such as the following are printed or displayed in instruction areas 28 and 30 on body portion 16:
  Place CPR Lifewrap on patient
  Line up mouthpiece to mouth
  Line up sternal diagram with patient's sternum, bottom first
  Place hands on Wrap hands
  Start CPR Connecting links 14, which join mask portion 12 to body portion 16, may be provided with fold lines 32 in order to facilitate lining up the sternal diagram on body portion 16 after mouthpiece 18 is aligned with the patient's mouth. In addition, upper AED fold line 34 and lower AED fold line 36 are provided to allow for folding of the template away from a portion of the patient's body in order to apply the defibrillator pads of a AED. Preferably, as shown, upper AED fold line 34 is located at the upper left side of body portion 16 and lower AED fold line 36 is located at the lower right side of body portion 16. It is also preferred that both the upper AED fold line and the lower AED fold line form an angle within the range of 60° to 70°, most preferably about 65° with baseline 38 of body portion 16.

CPR template 10 is formed of a pliable, translucent or transparent material, preferably medical grade polyethylene film having a thickness within the range of about 6 to about 10 mils. Generally, template 10 is sized and shaped to drape over and conform to an adult patient's body. Preferably, mask portion 12 has a height $MH_A$ of about 6.5 inches, and body portion 16 has a height $BH_A$ of about 16 inches. It is also preferred that body portion 16 has a top width $TW_A$ of about 16 inches, and a bottom width $BW_A$ of about 12 inches. In order to use CPR template 10, the device should be placed on the patient so that mouthpiece 18 aligns with the patient's mouth. Then the sternal diagram 40 printed on body portion 16 is aligned with the sternum of the patient, starting at the bottom of the sternum. Connecting links 14 may be folded or bunched as necessary to insure a proper fit. When the CPR template is properly placed on the patient, CPR may be begun.

CPR template 110 is essentially identical to template 10 except for size and the instructions printed in the instruction areas. Thus, CPR template 110, which is intended for use with a child, comprises generally triangular mask portion 112, one or more connecting links 114 (two are preferred) and a generally trapezoidal body portion 116. A conventional mask mouthpiece 118 is mounted in mask portion 112, and above that is located a "nose pinch" instruction/reminder 120. Preferably, mouthpiece 118 is located about 0.875 inches from baseline 122 of mask portion 112. It is also preferred that "nose pinch" instruction/reminder 120 is located so as to align with the nose of a typical child when the valve is aligned with the child's mouth, or at about 0.5 inches above mouthpiece 118. It is also preferred that CPR instructions such as the following are printed or displayed in instruction areas 124 and 126 on body portion 116:
  CPR Instructions
  1. Call 911/Get Help.
  2. Check for pulse/breathing.
  3. No breathing/pulse—Start CPR.
  Lay child down on flat, hard surface
  30 compressions 1.5 inches deep, fast and hard
  Tilt head, lift chin, pinch nose
  Slowly blow into mouth twice until chest rises
  Repeat 30 compressions to 2 breaths
  Continue until help arrives It is also preferred that template placement instructions such as the following are printed or displayed in instruction areas 128 and 130 on body portion 116:
  Place CPR Lifewrap on child
  Line up mouthpiece to mouth
  Line up sternal diagram with child's sternum, bottom first
  Place hands on Wrap hands
  Start CPR Connecting links 114, which join mask portion 112 to body portion 116, may be provided with fold lines 132 in order to facilitate lining up the sternal diagram on body portion 116 after mouthpiece 118 is aligned with the child's mouth. In addition, upper AED fold line 134 and lower AED fold line 136 are provided to allow for folding of the template away from a portion of the child's body in order to apply the defibrillator pads of a AED. Preferably, as shown, upper AED fold line 134 is located at the upper left side of body portion 116 and lower AED fold line 136 is located at the lower right side of body portion 116. It is also preferred that both the upper AED fold line and the lower AED fold line form an angle within the range of 60° to 70°, most preferably about 65° with baseline 138 of body portion 116.

CPR template 110 is formed of a pliable, translucent or transparent material, preferably medical grade polyethylene film having a thickness within the range of about 6 to about 10 mils. Generally, template 110 is sized and shaped to drape over and conform to a child's body. Preferably, mask portion 112 has a height $MH_c$ of about 5.125 inches, and body portion 116 has a height $BH_c$ of about 11.4 inches. It is also preferred that body portion 116 has a top width $TW_c$ of about 12 inches, and a bottom width $BW_c$ of about 6.75 inches. In order to use CPR template 110, the device should be placed on the child so that mouthpiece 118 aligns with the child's mouth. Then the sternal diagram 140 printed on body portion 116 is aligned with the sternum of the child, starting at the bottom of the sternum. Connecting links 114 may be folded or bunched as necessary to insure a proper fit. When the CPR template is properly placed on the child, CPR may be begun.

CPR template 210, which is intended for use with an infant, comprises generally rounded mask portion 212, one or more connecting links 214 (two are preferred) and a generally trapezoidal body portion 216. A conventional mask mouthpiece 218 is mounted in mask portion 212, and above that is located a "nose pinch" instruction/reminder 220. Preferably, mouthpiece 218 is located about 1 inch from baseline 222 of mask portion 212. It is also preferred that nose indicator 220 is located so as to align with the nose of a typical infant when the valve is aligned with the infant's mouth, or at about 1.5 inches above mouthpiece 218. It is also preferred that CPR instructions such as the following are printed or displayed in instruction areas 224 and 226 on body portion 216:
  CPR Instructions
  1. Call 911/Get Help.
  2. Check for pulse/breathing.
  3. No breathing/pulse—Start CPR.
  Lay infant down on flat, hard surface
  30 compressions 1.5 inches deep, fast and hard
  Tilt head, lift chin, pinch nose
  Slowly puff into mouth twice until chest rises
  Repeat 30 compressions to 2 puffs
  Continue until help arrives It is also preferred that template placement instructions such as the following are printed or displayed in instruction areas 228 and 230 on body portion 216:
  Place CPR Lifewrap on infant
  Line up mouthpiece to mouth
  Line up sternal diagram with infant's sternum, bottom first Place fingers on Wrap fingers
Start CPR Connecting links 214, which join mask portion 212 to body portion 216, may be provided with fold lines 232 in order to facilitate lining up the sternal diagram on body portion 216 after mouthpiece 218 is aligned with the infant's mouth. In addition, upper AED fold line 234 and lower AED fold line 236 are provided to allow for folding of the template away from a portion of the infant's body in order to apply the defibrillator pads of a AED. Preferably, as shown, upper AED fold line 234 is located at the upper left side of body portion 216 and lower AED fold line 236 is located at the lower right side of body portion 216. It is also preferred that both the upper AED fold line and the lower AED fold line form an angle within the range of 60° to 70°, most preferably about 65° with baseline 238 of body portion 216.

CPR template 210 is formed of a pliable, translucent or transparent material, preferably medical grade polyethylene film having a thickness within the range of about 6 to about 10 mils. Generally, template 210 is sized and shaped to drape over and conform to an infant's body. Preferably, mask portion 212 has a height $MH_I$ of about 4 inches, and body portion 216 has a height $BH_I$ of about 10.5 inches. It is also preferred that body portion 216 has a top width $TW_I$ of about 6 inches, and a bottom width $BW_I$ of about 4.5 inches. In order to use CPR template 210, the device should be placed on the infant so that mouthpiece 218 aligns with the infant's mouth. Then the sternal diagram 240 printed on body portion 216 is aligned with the sternum of the infant, starting at the bottom of the sternum. Connecting links 214 may be folded or bunched as necessary to insure a proper fit. When the CPR template is properly placed on the infant, CPR may be begun.

Although this description contains many specifics, these should not be construed as limiting the scope of the invention but as merely providing illustrations of the presently preferred embodiments thereof, as well as the best mode contemplated by the inventor of carrying out the invention. The invention, as described herein, is susceptible to various modifications and adaptations, as would be understood by those having ordinary skill in the art to which the invention relates.

What is claimed is:

1. A CPR template comprising: (a) a pliable mask portion that is adapted to be placed over the face of a person, said mask portion having a mouthpiece extending therethrough for use in administering rescue breaths; (b) a separate pliable body portion spaced apart from the mask portion and having: (i) a sternal diagram displayed thereon; (ii) an instructional area in which CPR instructions are displayed; (c) an elongate connecting link that spans between the mask portion and the separate body portion and links the mask portion to the body portion.

2. The CPR template of claim 1 wherein a nose pinch instruction/reminder is displayed above the mouthpiece of the mask portion.

3. The CPR template of claim 1 in which the connecting link is provided with fold lines to facilitate aligning the sternal diagram of the body portion with the patient's sternum after the mouthpiece of the mask portion is aligned with the patient's mouth.

4. The CPR template of claim 1 wherein: (a) the body portion is generally trapezoidal; (b) two connecting links join the mask portion to the body portion.

5. The CPR template of claim 4 wherein the mask portion is generally triangular.

6. The CPR template of claim 1 wherein the body portion includes an upper AED fold line and a lower AED fold line to allow for folding of the template away from a portion of the patient's body.

7. The CPR template of claim 6 wherein: (a) the body portion has a baseline; (b) both the upper AED fold line and the lower AED fold line form an angle within the range of 60 .degree. to 70 .degree. with the baseline of the body portion.

8. The CPR template of claim 6 wherein: (a) the body portion has a baseline; (b) both the upper AED fold line and the lower AED fold line form an angle of about 65 .degree. with the baseline of the body portion.

9. The CPR template of claim 1 wherein the pliable mask portion and the pliable body portion are formed of a translucent plastic material.

10. The CPR template of claim 9 wherein the pliable mask portion and the pliable body portion are formed of medical grade polyethylene film having a thickness within the range of about 6 to about 10 mils.

11. A CPR template comprising: (a) a pliable mask portion that is adapted to be placed over the face of a person, said mask portion having a mouthpiece extending therethrough for use in administering rescue breaths; (b) a pliable body portion having: (i) a sternal diagram displayed thereon; (ii) an instructional area in which CPR instructions are displayed; (c) a connecting link that joins the mask portion to the body portion, the connecting link including fold lines to facilitate aligning the sternal diagram of the body portion with the patient's sternum after the mouthpiece of the mask portion is aligned with the patient's mouth.

12. A CPR template comprising: (a) a pliable mask portion that is adapted to be placed over the face of a person, said mask portion having a mouthpiece extending therethrough for use in administering rescue breaths; (b) a pliable body portion having: (i) a sternal diagram displayed thereon; (ii) an instructional area in which CPR instructions are displayed, and (iii), an upper AED fold line and a lower AED fold line to allow for folding of the template away from a portion of the patient's body; and (c) a connecting link that joins the mask portion to the body portion.

13. The CPR template of claim 12 wherein: (a) the body portion has a baseline; (b) both the upper AED fold line and the lower AED fold line form an angle within the range of 60 .degree to 70 .degree with the baseline of the body portion.

14. The CPR template of claim 12 wherein: (a) the body portion has a baseline; (b) both the upper AED fold line and the lower AED fold line form an angle of about 65 .degree with the baseline of the body portion.

* * * * *